United States Patent
Deng et al.

(10) Patent No.: US 7,132,041 B2
(45) Date of Patent: Nov. 7, 2006

(54) METHODS OF DETERMINING THE CONCENTRATION OF AN ANALYTE IN A FLUID TEST SAMPLE

(75) Inventors: Yingping Deng, Fishers, IN (US); Amy H. Chu, Elkhart, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 270 days.

(21) Appl. No.: 10/770,199

(22) Filed: Feb. 2, 2004

(65) Prior Publication Data
US 2004/0154932 A1    Aug. 12, 2004

Related U.S. Application Data

(60) Provisional application No. 60/446,223, filed on Feb. 11, 2003.

(51) Int. Cl.
  G01N 27/26  (2006.01)
  G01N 33/50  (2006.01)
  C12Q 1/26   (2006.01)
(52) U.S. Cl. .................... 205/777.5; 205/792
(58) Field of Classification Search ............ 205/777.5, 205/792
See application file for complete search history.

(56) References Cited

U.S. PATENT DOCUMENTS

| | | | |
|---|---|---|---|
| 5,120,420 A | 6/1992 | Nankai et al. | 204/403 |
| 5,264,103 A | 11/1993 | Yoshioka et al. | 204/403 |
| 5,320,732 A | 6/1994 | Nankai et al. | 204/403 |
| 5,429,735 A | 7/1995 | Johnson et al. | 204/403 |
| 5,611,909 A | 3/1997 | Studer | |
| 5,620,579 A | 4/1997 | Genshaw et al. | 204/402 |
| 5,620,890 A | 4/1997 | Kamps-Holtzapple et al. | 435/345 |
| 5,653,863 A | 8/1997 | Genshaw et al. | 205/777.5 |
| 5,660,791 A | 8/1997 | Brenneman et al. | 422/58 |
| 5,798,031 A | 8/1998 | Charlton et al. | 204/403 |
| 6,576,117 B1 * | 6/2003 | Iketaki et al. | 205/777.5 |
| 6,841,052 B1 * | 1/2005 | Musho et al. | 204/401 |
| 2001/0042683 A1 | 11/2001 | Musho et al. | |

FOREIGN PATENT DOCUMENTS

| EP | 1 081 491 A1 | 3/2001 |
|---|---|---|
| EP | 1 262 769 A1 | 12/2002 |

OTHER PUBLICATIONS

U.S. Appl. No. 09/731,943, filed Dec. 8, 2000, Musho et al, (7 pages).

* cited by examiner

*Primary Examiner*—Alan Diamond
*Assistant Examiner*—Anthony Fick (57) ABSTRACT

A method of determining the concentration of an analyte in a fluid test sample that includes providing an electrochemical sensor adapted to measure the analyte in the test sample. The test sample sufficiently covers a counter and working electrode of the electrochemical sensor. A first potential is applied between the counter and working electrodes for a first predetermined time period and the current is measured and the time is recorded. After the first potential is removed or substantially reduced, a second potential is applied between the counter and working electrodes and the current is measured. The concentration of the analyte is determined in the test sample as a function of the current measured. An index is calculated and compared to at least one predetermined parameter to identify when a bias, if any, exceeds a threshold. An error signal or analyte concentration is displayed depending on the comparison.

28 Claims, 3 Drawing Sheets

METHODS OF DETERMINING THE CONCENTRATION OF AN ANALYTE IN A FLUID TEST SAMPLE

CROSS-REFERENCE TO RELATED APPLICATIONS

This application claims the benefit of the U.S. Provisional Application 60/446,223, filed on Feb. 11, 2003, which is hereby incorporated by reference in its entirety.

FIELD OF THE INVENTION

The present invention relates to methods using biosensors and, more specifically, methods of detecting bias in determining an analyte concentration in a fluid test sample caused by incompletely filled electrochemical sensors.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets. While the remainder of the disclosure herein will be directed towards determining glucose, it is to be understood that the methods of this invention may be used for determining other analytes upon selection of an appropriate enzyme.

There have been various methods implemented in the past that use biosensors (e.g., biochemical sensors) to determine the quantity of a specific component (analyte) in a fluid sample. Some examples of these biosensors, including electrochemical sensors, are disclosed in U.S. Pat. Nos. 5,120,420, 5,264,103 and 5,620,579, and U.S. Publication No. 20010042683.

Some drawbacks with existing methods that use electrochemical sensors may occur when an insufficient amount of the fluid sample is present. These drawbacks occur when counter and working electrodes of the electrochemical sensors are not completely covered with the fluid sample, resulting in an incomplete current flowing across the electrodes. Since the amount of analyte (e.g., glucose) detected by the electrochemical sensor is directional proportional to the current flowing through the detection meter, failure to completely cover the electrochemical sensor's electrodes may result in a bias of the blood sample's analyte (e.g., glucose concentration).

It would be desirable to provide a method that detects when there is an insufficient amount of fluid sample and report such a condition as an error to the user. It also would be desirable to provide a method that detects electrochemical sensors with an abnormal rehydration process, because of an insufficient sample to completely re-hydrate the chemistry of the electrochemical sensor. It would be desirable to provide a method that determines an insufficient amount of fluid sample exists even when the electrodes of the electrochemical sensors are sufficiently covered. It would also be desirable to report such conditions as errors to the user if the bias of the analyte concentration exceeds a predetermined threshold caused by, for example, solution movement in incompletely filled sensors or abnormal re-hydration kinetics.

SUMMARY OF THE INVENTION

According to one method of determining the concentration of an analyte in a fluid test sample, an electrochemical sensor adapted to measure the analyte in the fluid test sample is provided. The electrochemical sensor has a counter electrode and a working electrode. The counter and working electrodes of the electrochemical sensor are sufficiently covered by the fluid test sample. A first potential is applied between the counter electrode and working electrode for a first predetermined time period. The current is measured between the counter electrode and working electrode at a plurality of times during the first predetermined time period. The times of the measurements during the first predetermined time period is recorded. The first potential is removed or substantially reduced between the counter electrode and working electrode for a second predetermined time period. A second potential is applied between the counter electrode and working electrode for a third predetermined time period. The current is measured between the counter electrode and working electrode at least once during the third predetermined time period.

The concentration of the analyte in the fluid test sample is determined as a function of the current measured. An index is calculated using at least two of the following: a measured current and recorded time of the first predetermined time period, and the measured current of the third predetermined time period. The index is compared to at least one predetermined parameter related to the determined concentration of analyte in the fluid test sample to identify when a bias, if any, exceeds a predetermined threshold. An error signal or an analyte concentration is displayed depending on the comparison between the index and the at least one of the predetermined parameter.

According to another method of determining the concentration of an analyte in a fluid test sample, an electrochemical sensor adapted to measure the analyte in the fluid test sample is provided. The electrochemical sensor has a counter electrode and a working electrode. The counter and working electrodes of the electrochemical sensor are sufficiently covered by the fluid test sample. A first potential is applied between the counter electrode and working electrode for a first predetermined time period. The current is measured between the counter electrode and working electrode a plurality of times during the first predetermined time period. The times of the measurements during the first predetermined time period is recorded. The first potential is removed or substantially reduced between the counter electrode and working electrode for a second predetermined time period. A second potential is applied between the counter electrode and working electrode for a third predetermined time period. The current is measured between the counter electrode and working electrode at least once during the third predetermined time period.

The concentration of the analyte in the fluid test sample is determined as a function of the current measured. An index (I) is calculated by solving the equation:

$$I = (I_{rt}/I_{bmax}) * T_{bmax}$$

where $I_{rt}$ = the last measurement of the current during the third predetermined time period, $I_{bmax}$ = the highest current measured during the first predetermined time period, and $T_{bmax}$ = the time of the highest measured current is measured during the first predetermined time period.

The index is compared to at least one predetermined parameter related to the determined concentration of analyte in the fluid test sample to identify when a bias, if any, exceeds a predetermined threshold. An error signal or an analyte concentration is displayed depending on the comparison between the index and the at least one of the predetermined parameter.

According to a further method of determining the concentration of an analyte in a fluid test sample, an electrochemical sensor adapted to measure the analyte in the fluid test sample is provided. The electrochemical sensor has a counter electrode and a working electrode. The counter and working electrodes of the electrochemical sensor are sufficiently covered by the fluid test sample. A first potential is applied between the counter electrode and working electrode for a first predetermined time period. The current is measured between the counter electrode and working electrode at a plurality of times during the first predetermined time period. The times of the measurements during the first predetermined time period is recorded. The first potential is removed or substantially reduced between the counter electrode and working electrode for a second predetermined time period. A second potential is applied between the counter electrode and working electrode for a third predetermined time period. The current is measured between the counter electrode and working electrode at least once during the third predetermined time period.

The concentration of the analyte in the fluid test sample is determined as a function of the current measured. An index is calculated using a measured current and recorded time of the first predetermined time period, and the measured current of the third predetermined time period. The index is compared to at least one predetermined parameter related to the determined concentration of analyte in the fluid test sample to identify when a bias, if any, exceeds a predetermined threshold. An error signal or an analyte concentration is displayed depending on the comparison between the index and the at least one of the predetermined parameter.

According to yet another method of determining the concentration of an analyte in a fluid test sample, an electrochemical sensor adapted to measure the analyte in the fluid test sample is provided. The electrochemical sensor has a counter electrode and a working electrode. The counter and working electrodes of the electrochemical sensor are sufficiently covered by the fluid test sample. A potential is applied between the counter electrode and working electrode for a predetermined time period. The current is measured between the counter electrode and working electrode at a plurality of times during the predetermined time period. The times of the measurements during the predetermined time period is recorded. The concentration of the analyte in the fluid test sample is determined as a function of the current measured. An index is calculated using a selected measured current and recorded time of the predetermined time period. The index is compared to at least one predetermined parameter related to the determined concentration of analyte in the fluid test sample to identify when a bias, if any, exceeds a predetermined threshold. An error signal or an analyte concentration is displayed depending on the comparison between the index and the at least one of the predetermined parameter.

While the invention is susceptible to various modifications and alternative forms, specific embodiments thereof has been shown by way of example in the drawing and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DETAILED DESCRIPTION OF THE ILLUSTRATED EMBODIMENT

The present invention relates to methods using biosensors and, more specifically, methods of detecting bias in determining the concentration of an analyte caused by incompletely filled biosensors (i.e., an under-fill condition). By detecting high-biased analyte results caused by, for example, sample movement inside an incompletely filled biosensor, the biosensor's performance can be improved. Other abnormal conditions may include an insufficient sample to completely dissolve the sensor's chemistry. The biosensor's performance is improved by reporting such results as an under-filled error to the user. It is desirable to be able to detect and report an under-filled error that occurs when one of the electrodes of an under-filled sensor is not contacted with the fluid test sample. An example of such a condition is when the fluid test sample is sufficient to make contact between the working the counter electrodes, but insufficient to completely fill the capillary (e.g., about 3.5 µL). The bias may occur when blood moves up the capillary when the sensor is pulled away from the whole blood samples due to the breaking of the meniscus and capillary action. The magnitude of the bias on the final glucose reading depends on the percentage of blood volume in the sensor capillary and the time when the sensor is pulled away from the sample drop.

As discussed above, the analyte to be tested may be glucose in a whole blood sample. The analyte (e.g., glucose) concentration of the fluid test sample (e.g., whole blood sample) may be determined using an amperometric monitoring system.

Electrochemical Sensor

To determine the glucose concentration in a whole blood sample, an electrochemical sensor according to one embodiment is provided. It is important that the electrochemical sensor provides reliable and reproducible measurements. According to one embodiment, the electrochemical sensor in the present invention may be that described in U.S. patent application published as 20010042683 on Nov. 22, 2001 and entitled Electrochemical-Sensor Design, which is incorporated by reference in its entirety.

Figure 1:
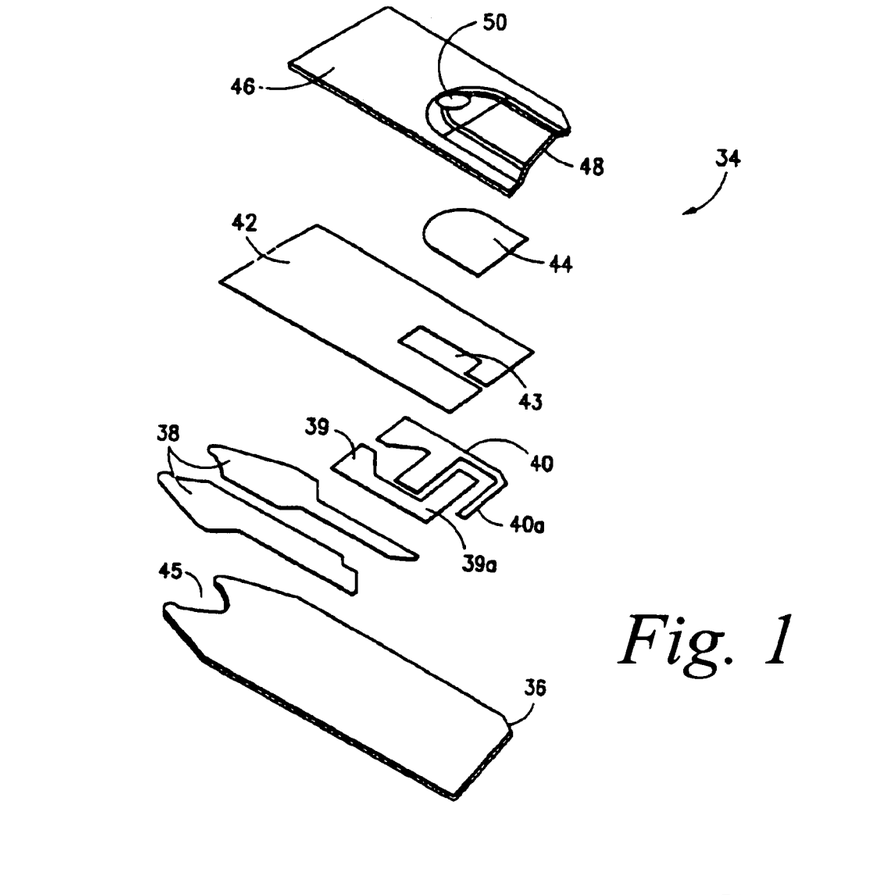
FIG. 1 is an exploded view of an electrochemical sensor according to one embodiment that may be used in a method of the present invention.
Figure 2:
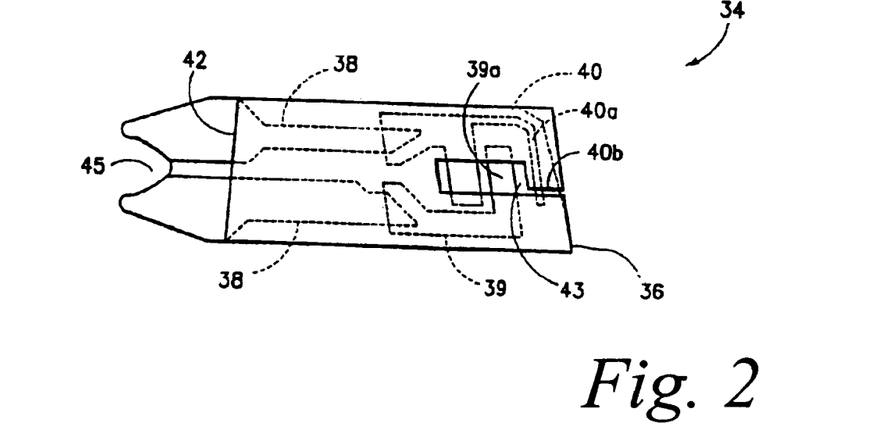
FIG. 2 is a sensor base and those elements that are applied directly to the base of the sensor in FIG. 1.

An example of an electrochemical sensor described in U.S. patent application published as 20010042683 is depicted in FIG. 1. Referring to FIG. 1, a sensor 34 comprises an insulating base 36 upon which is printed in sequence (typically by screen printing techniques), an electrical conductor pattern 38, an electrode pattern (portions 39 and 40), an insulating (dielectric) pattern 42, and a reaction layer 44. The base of the electrochemical sensor provides a flow path for the fluid test sample. The sensor base is shown in FIG. 2 in which all of the elements on the base are shown in the same plane.

The function of the reaction layer 44 is to convert glucose, or another analyte in the fluid test sample, stoichiometrically into a chemical species which is electrochemically measurable, in terms of electrical current it produces, by the components of the electrode pattern. The reaction layer 44 generally contains a biosensing or reagent material, such as an enzyme, and an electron acceptor. More specifically, the reaction layer 44 contains an enzyme that reacts with the analyte to produce mobile electrons on the electrode pattern and an electron acceptor (e.g., a ferricyanide salt) to carry the mobile electrons to the surface of the working electrode. The electron acceptor may be referred to as a mediator in which the mediator is reduced in response to a reaction between the analyte and the enzyme. The enzyme in the reaction layer may be combined with a hydrophilic polymer, such as polyethylene oxide. An enzyme that may be used to react with glucose is glucose oxidase. It is contemplated that other enzymes may be used such as glucose dehydrogenase.

The two portions 39, 40 of the electrode pattern provide the respective working and counter electrodes necessary to electrochemically determine the analyte. The working electrode typically comprises an enzyme that reacts with the analyte. The working and counter electrodes may be configured such that the major portion of the counter electrode is located downstream (in terms of the direction of fluid flow along the flow path) from the exposed portion of the working electrode 39a. This configuration allows the test fluid sample to completely cover the exposed portion of the working electrode for all cases in which an undetected partial fill has occurred.

Counter electrode sub-element 40a, however, is positioned up-stream from working electrode upper element 39a so that when an inadequate amount of the test fluid sample (e.g., a whole blood sample) to completely cover the working electrode enters the capillary space, an electrical connection forms between counter electrode sub-element 40a and exposed portion of the working electrode 39a due to the conductivity of the whole blood sample. The area of the counter electrode, however, that is available for contact by the whole blood sample is so small that only a very weak current can pass between the electrodes and, thus, through the current detector. By programming the current detector to give an error signal when the received signal is below a certain pre-determined level, the sensor device informs the user that insufficient blood has entered the sensor's cavity and that another test should be conducted. While the particular dimensions of the electrodes are not critical, the area of the counter electrode sub-element 40a is typically less than about 10% than that of the working electrode and, more specifically, less than about 6%. This element should be made as small as possible in view of the restraints of the screen printing process.

It is also contemplated that the reaction layer 44 may be removed from contact with counter electrode sub-element 40a. This is accomplished by producing a screen that does not print reagent ink over the counter electrode sub-element 40b. This serves the purpose of starving the sub-element for reagent, thereby not allowing it to function as a proper counter electrode, so that an error condition is achieved when the test fluid sample fails to contact the bulk of the counter electrode 40. While sub-element 40a is depicted as being physically connected to, and therefore part of, the counter electrode 40, such physical connection is not critical. Such sub-element may be physically disconnected from the rest of the counter electrode provided that it has its own connector and the sensor is equipped with a third contact to the detector.

The working and counter electrodes include electrode ink. The electrode ink, which is generally about 14µ (0.00055") thick, typically contains electrochemically active carbon. Components of the conductor ink may be a mixture of carbon and silver that is chosen to provide a low chemical resistance path between the electrodes and the meter with which they are in operative connection via contact with the conductive pattern at a fish-tail end 45 of the sensor. The counter electrode may be comprised of silver/silver chloride although carbon is preferred. To enhance the reproducibility of the meter reading, the dielectric pattern insulates the electrodes from the fluid test sample except in a defined area near the center of the electrode pattern 43. A defined area is important in this type of electrochemical determination because the measured current depends on the analyte concentration and the area of the reaction layer that is exposed to the analyte-containing test sample.

A typical dielectric layer 42 comprises a UV-cured acrylate modified polymethane that is about 10µ (0.0004") thick. A lid or cover 46 is adapted to mate with the base to form a space to receive the fluid test sample in which the counter and working electrodes are situated. The lid 46 provides a concave space 48, and is typically formed by embossing a flat sheet of deformable material. The lid 48 is punctured to provide an air vent 50 and joined to the base 36 in a sealing operation. The lid and base can be sealed together by sonic welding in which the base 36 and lid 46 are first aligned and then pressed together between a vibratory heat sealing member or horn and a stationary jaw. The horn is shaped such that contact is made only with the flat, non-embossed regions of the lid. Ultrasonic energy from a crystal or other transducer is used to excite vibrations in the metal horn. This mechanical energy is dissipated as heat in the polymeric joint allowing the bonding of the thermoplastic materials. The embossed lid and base may be joined by using an adhesive material on the underside of the lid. The method of joining the lid and base are more fully described in U.S. Pat. No. 5,798,031 which is incorporated herein by reference in its entirety.

Suitable materials for the insulating base 36 include polycarbonate, polyethylene terephthalate, dimensionally-stable vinyl and acrylic polymers, and polymer blends such as polycarbonate/polyethylene terephthalate and metal foil structures (e.g., a nylon/aluminum polyvinyl chloride laminate). The lid is typically fabricated from a deformable polymeric sheet material such as polycarbonate, or an embossable grade of polyethylene terephthalate, glycol modified polyethylene terephthalate or a metal foil composition (e.g., an aluminum foil structure). The dielectric layer may be fabricated from an acrylate-modified polyurethane that is curable by UV light or moisture or a vinyl polymer that is heat curable.

It is contemplated that other electrochemical sensors may be used in the present invention. Examples of an electrochemical sensor that can be used to measure glucose concentrations are those used in Bayer Corporation's Glucometer DEX® and ELITE® systems. More details on such an electrochemical sensor may be found in U.S. Pat. Nos. 5,120,420 and 5,320,732 which are both incorporated by reference in their entirety. One or more of the electrochemical sensors may be purchased from Matsushita Electric Industrial Company. Another electrochemical sensor is disclosed in U.S. Pat. No. 5,798,031, which is incorporated by reference in its entirety. A further example of an electrochemical sensor that may be used in an amperometric monitoring system is disclosed in U.S. Pat. No 5,429,735. It is contemplated that other biosensors may be used in the present invention.

The electrochemical sensors may be located in a blood glucose sensor dispensing instrument that is adapted to have loaded therein a sensor pack that includes a plurality of sensors or testing elements. Each of the sensors is adapted to be ejected from the sensor pack. One example of a sensor pack loaded in a sensor dispensing instrument is disclosed in U.S. Pat. No. 5,660,791. It is contemplated that the electrochemical sensors may be stored in other apparatus such as bottles.

Methods of the Present Invention

A method of determining the concentration of an analyte in a fluid test sample of the present invention may include using one of the electrochemical sensors described above (e.g., sensor 34). The electrochemical sensor includes a counter electrode and a working electrode. It is contemplated that other electrochemical sensors may be used than described in connection with FIGS. 1 and 2.

Figure 3:
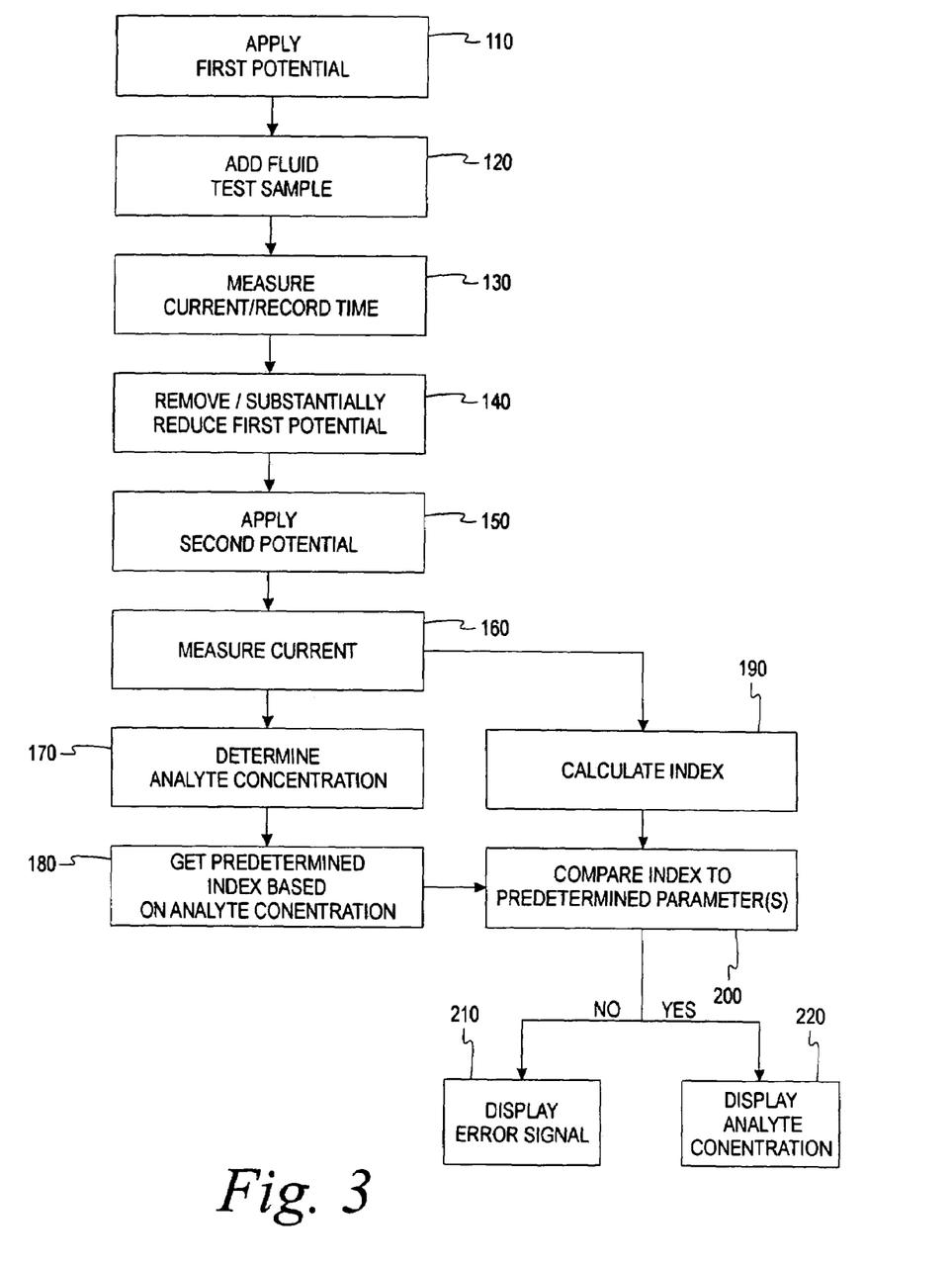
FIG. 3 is flowchart depicting a sequence of steps to determine the concentration, of an analyte in a fluid test sample according to one method of the present invention.

Referring to FIG. 3, step 110 applies a first potential between the counter electrode and working electrode. The fluid test sample with analyte is added so as to contact the electrochemical sensor in step 120. The first potential is applied between the counter and working electrodes for a first predetermined time period. The first potential is generally from about 100 to about 600 mV and, more typically, from about 300 to about 500 mV.

The current is measured between the counter electrode and working electrode at a plurality of intervals, and the times of the measurements are recorded during the first predetermined time period during step 130. The first predetermined time period is generally from about 2 to about 30 seconds and, more typically, from about 5 to about 15 seconds. The current during the first predetermined time period may be measured in regular intervals that may vary in duration. For example, the current during the first predetermined time period is generally measured in regular intervals of from about 0.1 to about 3 seconds, and, more typically, from about 0.2 to about 0.5 seconds. During the measuring of the current, the time of such measurements is recorded. The first predetermined time period is referred to as the "burn-off" period.

During step 140, the first potential between the counter electrode and working electrode is removed or substantially reduced for a second predetermined time period. The second predetermined time period is generally from about 2 to about 20 seconds and, more typically, from about 5 to about 15 seconds. The second predetermined time period is referred to as the "wait" or "incubation" period.

A second potential between the counter electrode and working electrode is applied for a third predetermined time period in step 150. The second potential is generally from about 100 to about 600 mV and, more typically, from about 300 to about 500 mV. The current is measured between the counter and working electrodes during the third predetermined time period in step 160. The third predetermined time period is generally from about 2 to about 30 seconds and, more typically, from about 5 to about 15 seconds. The current during the third predetermined time period may be measured in regular intervals that may vary in duration. For example, the current is generally measured in regular intervals of from about 0.1 to about 3 seconds, and, more typically, from about 0.2 to about 0.5 seconds. The third predetermined time period is referred to as "read" period. According to another method, the second and third predetermined time periods may be eliminated.

According to one method, the concentration of the analyte is determined in the fluid test sample as a function of the current measured during the third predetermined time period in step 170. It is contemplated, however, that the concentration of the analyte may be determined as a function of the current measured during the first predetermined time period.

To assist in determining if an under-fill condition is present when the electrodes of the electrochemical sensor are not sufficiently covered by the test fluid sample, the analyte concentration may be compared to at least one factor, such as the k-factor and/or read-to-burn ratio. The electrochemical sensor is configured so that in the event of an under-fill condition, the result will be affirmative as opposed to a neutral response, i.e. a failure of the detector to give, any signal. Thus, for example, when the amount of the test fluid sample that enters the capillary space is sufficient to cover the counter electrode sub-element 40a or 40b and that portion of the working electrode 39a which lies upstream from the main portion of the counter electrode 40, the detector will sense a current but the current will be weaker than if the working and counter electrodes were completely or sufficiently covered with the test fluid sample. The detector may be connected with the reading means to display an error signal to the user when an under-fill condition occurs.

There are provided means for sensing certain characteristics of the current over time that are used along with the absolute current level to determine if an error condition has occurred. This is accomplished by algorithmically programming the meter to detect the under-fill condition by measuring the current at a definite time period after the test fluid has electrically connected the sub-element of the counter electrode with the working electrode. The ratio of the currents for the two measurements is used to determine if the sensor has filled properly. For example, the current is measured at 5 and 10 seconds after applying the driving potential to the circuit, and these two currents are converted into a ratio. This ratio and the current reading at 10 seconds are used to determine if the sensor's capillary space has filled properly.

A sample calculation is as follows: three current measurements are made during the test sequence according to one method: (a) at the end of an initial period known as the "burn-off" period in which the driving potential has been applied for a first predetermined time period (e.g., 10 seconds denoted as $I_{b10}$); (b) when the potential is applied and measured during the third predetermined time interval or "read" period at, for example, 5 seconds ($I_{r5}$), and (c) at the end of the third predetermined time period (e.g., 10 seconds) known as the "read" period denoted as $I_{r10}$. It is contemplated that the time periods may vary from the exemplary times above. Two parameters may be determined from these three current measurements. At least one of these two parameters is used to determine if the sensor's capillary space has filled properly. The first parameter is the decay factor, k, which describes the shape of current time course. The second parameter is a ratio that characterizes the rate of decay in the current level during the read phase.

The decay factor, k, is defined as:

$$k = ln(I_{r5}) - ln(I_{r10})/(ln(10) - ln(5)) \qquad \text{Equation A}$$

The Read-to-Burn ratio, R/B, is defined as:

$$R/B = I_{r10}/I_{b10} \qquad \text{Equation B}$$

One example of criteria for an under-fill condition using these two parameters may be as follows:

If $k<0.227$ or $k>0.497$; or (1)

If $R/B<0.263$ or $R/B>1.263$. (2)

It is contemplated that the numbers of this criteria may vary for the decay factor, k, and the Read-to-Burn ratio, R/B, in determining whether an under-fill condition is present. An under-filled sensor produced the following three current measurements:

An example using these parameters with an under-filled condition is as follows:

$I_{b10}$=505.1 nA, $I_{r5}$=656.5 nA, and $I_{r10}$=561.8 nA.

The decay factor and Read-to-Burn ratio were calculated from these current measurements:

Decay factor $$k = \frac{\ln(I_{r5}) - \ln(I_{r10})}{\ln(10) - \ln(5)} = \frac{\ln(656.5) - \ln(561.8)}{\ln(10) - \ln(5)} = 0.22$$

Read-to-Burn ratio $$R/B = I_{r10}/I_{b10} = 561.8/505.1 = 1.11$$

These two parameters were used to detect the following error conditions:

k<0.227 or k>0.497 at this glucose readback level. True, because k=9.22<0.227;

R/B<0.263 or R/B>1.263 at this glucose readback level. False, because R/B=1.11>0.263 and <1.263.

By providing a device which gives a positive (as opposed to a neutral) response in the event of an under-fill condition when the electrodes of the electrochemical sensor are not sufficiently covered by the test fluid sample, the user will recognize that the abortive function of the test is a result of too little blood entering the capillary space, rather than some other malfunction having caused the anomalous result. Such a comparison works well when the counter electrode of an under-filled sensor is not contacted with the blood sample. The counter electrode (without movement of the whole blood sample) is not typically contacted with the blood sample in DEX system when the whole blood sample is below about 2.5 µL or 2.0 µL.

To improve the detection of certain under-fill conditions (e.g., a condition where the whole blood sample is moving such that the sensor capillary is incompletely filled but the whole blood sample is in contact with the counter electrode), an index is calculated in the present invention. An index is calculated in step 190 according to one process by using at least two of the following: one measured current and recorded time during the first predetermined time period, and at least one measured current of the third time period.

One example of an index that may be used in the present invention is by solving Equation C which uses all three variables:

$$\text{Index } (I) = (I_{rt}/I_{bmax}) * T_{bmax} \qquad \text{Equation C}$$

where:

$I_{rt}$=a current measured during the first or third predetermined time period (e.g., the last measurement of the current during the third predetermined time period), $I_{bmax}$=the highest current measured during the first predetermined time period, and $T_{bmax}$=the time when the highest current is measured during the first predetermined time period.

It is contemplated that other equations may be used to determine an index in the present invention that may use less than the above three variables. For example, two of these variables (a measured current and recorded time of the first determined time period and the measured current of the third predetermined time period) may be used to determine an appropriate index. One example of such is to determine an appropriate index by using the slope of the measured current and recorded time of the first determined time period. Alternatively, it is contemplated that other indices may be created using the slope of (a) the measured current of the first predetermined time period and the measured current of the third predetermined time period, or (b) the recorded time of the first predetermined time period and the measured current of the third predetermined time period.

In step 200, the index is compared to at least one predetermined parameter related to the determined concentration of analyte in the fluid test sample to identify when the bias exceeds a predetermined threshold, which is obtained from step 180. The predetermined parameter(s) is typically stored in the meter.

Depending on whether the index is within at least one of the predetermined parameter, either an error signal is displayed (step 210) or the analyte concentration is displayed (step 220). According to one process, an error signal is displayed when the index is not within the at least one predetermined parameter and the analyte concentration is displayed when the index is within the at least one predetermined parameter. Alternatively, the error signal may be displayed when the index is within the at least one predetermined parameter and the analyte concentration is displayed when the index is not within the at least one predetermined parameter.

Figure 4:
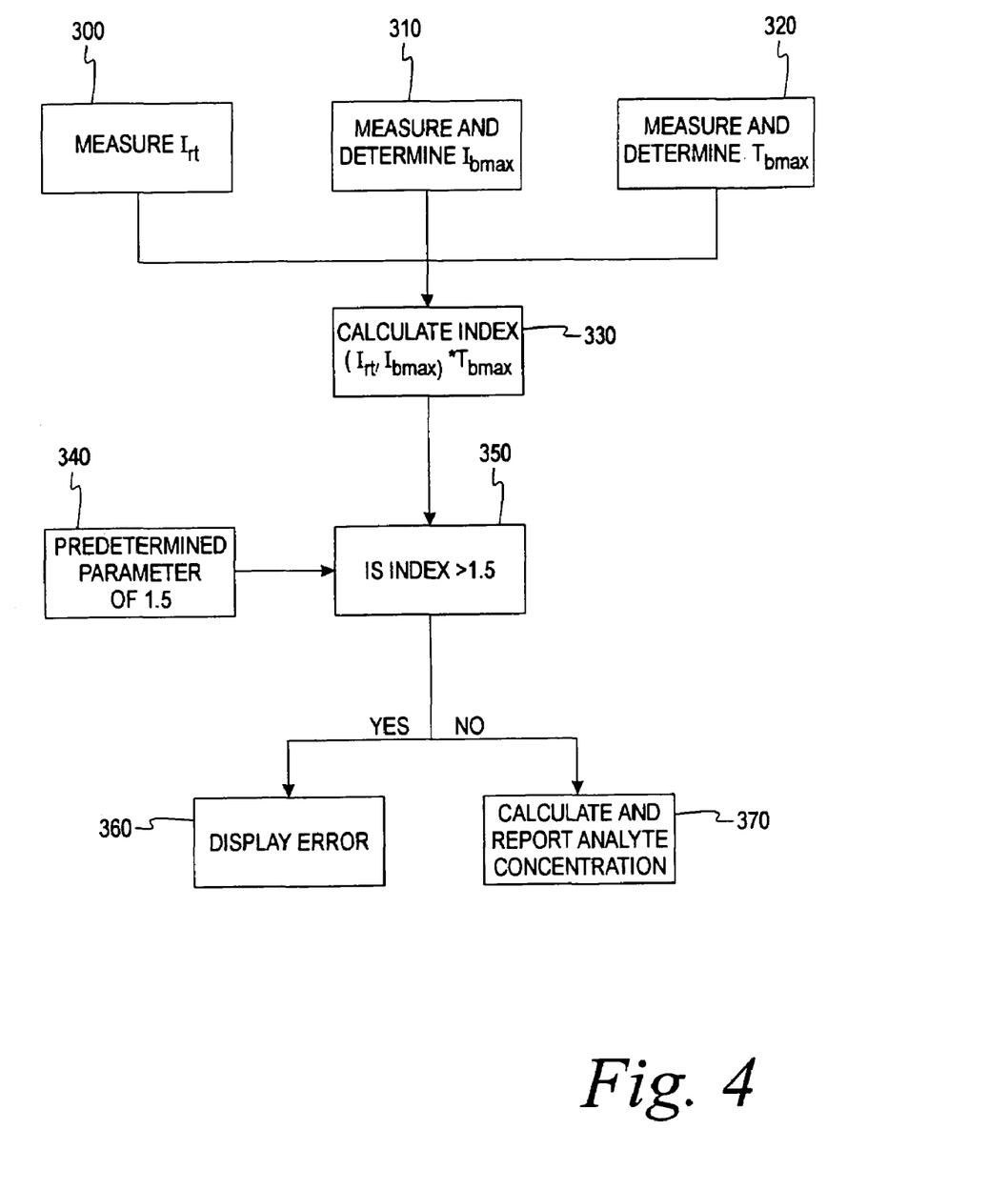
FIG. 4 is a flowchart depicting a sequence of steps to determine an index and report an under-fill condition to the user according to one method of the present invention.

An example of determining an index and comparing it with a predetermined parameter is shown in FIG. 4. The index is calculated as described above in Equation C in step 330 using the $I_{rt}$=the last measurement of the current during the third predetermined time period from step 300, $I_{bmax}$=the highest current measured during the first predetermined time period from step 310, and $T_{bmax}$=the time when the highest current is measured during the first predetermined time period from step 320.

The index from step 330 is compared in step 350 to a predetermined parameter taken from step 340. In this example, the predetermined parameter is 1.5. It is contemplated that the predetermined parameter may be different than shown in step 340. The predetermined parameter is related to the level of glucose concentration. If the index is greater than the predetermined parameter of 1.5, then a display error is indicated at step 360. If the index is less than or equal to 1.5, then the analyte concentration will be calculated and reported to the user in step 370.

The method for determining the analyte concentrations (e.g., glucose concentrations) may be performed in disposable self-testing systems. The disposable self-testing systems are often used by end consumers, especially those who are diabetic. Alternatively, the method for determining the analyte concentrations (e.g., glucose concentrations) may be performed in clinical analyzers. Clinical analyzers are often used in hospitals or clinics.

The testing end of the sensor is adapted to be placed into contact with the fluid sample (e.g., a whole blood sample) to be tested. The whole blood sample may be generated by a lancing device such as a microlet. The lancing device may obtain blood by, e.g., pricking a person's finger. According to one process, the whole blood sample may be prepared for testing by (a) removing the electrochemical sensor from a packet, (b) placing the electrochemical sensor into a glucose concentration measuring instrument, (c) generating a whole blood sample, and (d) bringing the sensor and the whole blood sample into contact wherein the blood is generally drawn into the sensor by capillary action.

According to one process, a whole blood sample is introduced into the space via an introducing port. Gas is discharged from the space by the inflow of the whole blood sample via a discharge port. It is believed that the glucose in the whole blood sample reacts with the enzyme (e.g., glucose oxidase carried on the electrodes to produce gluconic acid). A voltage is applied (e.g., 600 mV) between the electrodes and the electrode for measurement is polarized in the anode direction. By applying a voltage in the anode direction, an oxidizing current for the produced hydrogen peroxide is obtained. This current level corresponds to the concentration of glucose in the whole blood sample.

EXAMPLES

Several experiments were performed to show the effects of the glucose concentrations of a whole blood sample using a under-filled test sensors (see Table 1). Also, several experiments were performed using a whole blood sample in a proper filled condition (see Table 2).

Table 1 Testing Procedure

Whole blood samples of 3 µL were tested 15 times with various solution movement during the testing. In other words, some samples moved slightly, while others were moved to a greater extent. The whole blood samples were taken from the same source and, thus, had about the same glucose concentration.

The testing was performed using the following steps. First, a positive potential of 400 mV was applied between the working electrode and the counter electrode of the electrochemical sensor. The electrochemical sensor that was used was taken from Bayer Corporation's Glucometer DEX® system. A 3 µL whole blood sample was added to and contacted the electrochemical sensor. The current was measured between the working and the counter electrodes every 0.3 second for 10 seconds during the "burn" period. This current is referred to as the burn current. The respective times were also recorded that corresponded to the measurements of the burn current. The potential between the working and counter electrodes was removed, resulting in an open circuit for a time period of 10 seconds. This time period is referred to as the "wait" or "incubation" period. A positive potential of 400 mV was re-applied between the working and the counter electrodes of the electrochemical sensor. The current was measured between the working electrode and the counter electrode every 0.3 second for 10 seconds during the "read" period. This current is referred to as the read current. The read current was used to determine the glucose concentration of the whole blood sample.

This glucose calculation was then compared to predetermined parameters of k-factor and the read-to-burn ratio to determine if the blood sample amount was not sufficient. These ratios were calculated in the same manner as described above in the application in Equations A and B.

The index was calculated as described above in Equation C and then compared to a predetermined index of 1.5. If the index was greater than 1.5, then an error was displayed. If the index was less than or equal to 1.5, then the analyte concentration was reported. The test results are shown in Table 1 below.

The % bias from 10 µL, which is an example of 100% filled condition, was calculated as follows in Equation D:

$$(Glucose_{any\ underfil\ volume} - Glucose_{10\ uL})/Glucose_{10\ uL} * 100 \quad \text{Equation D}$$

The 10 µL sample was used to ensure that the sensors were 100% filled.

TABLE 1

| Replicate No. | $T_{bmax}$ (sec) | $I_{bmax}$ (nA) | $I_{r10}$ (nA) | Index | % Bias | Error out (yes/no) |
|---|---|---|---|---|---|---|
| 1 | 0.3 | 4230 | 1407 | 0.10 | 1.74 | No |
| 2 | 0.3 | 6561 | 1321 | 0.06 | −4.48 | No |
| 3 | 5.7 | 5771 | 1472 | 1.45 | 6.44 | No |
| 4 | 7.8 | 4105 | 1552 | 2.95 | 12.22 | Yes |
| 5 | 2.1 | 3809 | 1406 | 0.78 | 1.66 | No |
| 6 | 0.9 | 5078 | 1410 | 0.25 | 1.95 | No |
| 7 | 1.8 | 14115 | 1441 | 0.18 | 4.95 | No |
| 8 | 1.5 | 11557 | 1444 | 0.19 | 5.17 | No |
| 9 | 8.4 | 4452 | 1579 | 2.98 | 15.00 | Yes |
| 10 | 2.7 | 8631 | 1477 | 0.46 | 7.57 | No |
| 11 | 1.5 | 11364 | 1434 | 0.19 | 4.44 | No |
| 12 | 0.9 | 5210 | 1360 | 0.23 | −0.95 | No |
| 13 | 2.4 | 9261 | 1451 | 0.38 | 5.68 | No |
| 14 | 1.8 | 11665 | 1403 | 0.22 | 2.18 | No |
| 15 | 5.7 | 5627 | 1511 | 1.53 | 10.05 | Yes |

As can be seen in Table 1 above, Replicate Nos. 4, 9 and 15 had indices greater than 1.5 and, thus, produced an error signal to the user. On the other hand, Replicate Nos. 1–3, 5–8 and 10–14 did not have indices greater than 1.5 and, thus, did not display an error signal to the user. This test indicates that when a sensor is incompletely filled (such as with a 3 µL whole blood sample), then high biased results may occur that are unacceptable. This was confirmed when Replicate Nos. 4, 9 and 15, independent of the index and the resulting error signal, had % biases greater than 10%. In these examples, the decay factor, k, and the Read-to-Burn ratio, R/B, would be within their normal boundaries in determining whether an under-fill condition is present because the counter and working electrodes would be sufficiently covered with a 3 µL whole blood sample. In other words, using k and/or R/B would not have detected the high biased results.

Table 2 Testing Procedure

Whole blood samples of 10 µL were tested 15 times without any solution movement during sampling. The whole blood samples were taken from the same source and, thus, had about the same glucose concentration. The testing procedure was the same as set forth above in the testing procedure of Table 1.

TABLE 2

| Replicate No. | $T_{bmax}$ (sec) | $I_{bmax}$ | $I_{r10}$ | Index | % Bias | Error out (yes/no) |
|---|---|---|---|---|---|---|
| 1 | 2.1 | 4133 | 1401 | 0.71 | 1.30 | No |
| 2 | 2.7 | 3402 | 1398 | 1.11 | 1.08 | No |
| 3 | 1.2 | 3878 | 1291 | 0.40 | −6.65 | No |

TABLE 2-continued

| Replicate No. | T$_{bmax}$ (sec) | I$_{bmax}$ | I$_{r10}$ | Index | % Bias | Error out (yes/no) |
|---|---|---|---|---|---|---|
| 4 | 2.1 | 4017 | 1441 | 0.75 | 4.19 | No |
| 5 | 1.8 | 4041 | 1409 | 0.63 | 1.88 | No |
| 6 | 2.4 | 3686 | 1360 | 0.89 | −1.66 | No |
| 7 | 1.5 | 4313 | 1423 | 0.49 | 3.64 | No |
| 8 | 1.5 | 4860 | 1318 | 0.41 | −4.01 | No |
| 9 | 1.2 | 4915 | 1392 | 0.34 | 1.38 | No |
| 10 | 1.5 | 4546 | 1389 | 0.46 | 1.17 | No |
| 11 | 1.8 | 4285 | 1390 | 0.58 | 1.24 | No |
| 12 | 1.5 | 4638 | 1324 | 0.43 | −3.57 | No |

As can be seen in Table 2 above, none of the Replicate Nos. 1–15 had indices greater than 1.5 and, thus, none produced an error signal to the user. This showed that a completely filed whole blood sample without solution movement did not produce an error signal to the user using the calculated index and the predetermined parameter of 1.5.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of determining the concentration of an analyte in a fluid test sample, the method comprising the acts of:
   providing an electrochemical sensor adapted to measure the analyte in the fluid test sample, the electrochemical sensor having a counter electrode and a working electrode;
   sufficiently covering the counter and working electrodes of the electrochemical sensor with the fluid test sample;
   applying a first potential between the counter electrode and working electrode for a first predetermined time period;
   measuring the current between the counter electrode and working electrode at a plurality of intervals during the first predetermined time period;
   recording the times of at least one measurement during the first predetermined time period;
   removing or substantially reducing the first potential between the counter electrode and working electrode for a second predetermined time period;
   applying a second potential between the counter electrode and working electrode for a third predetermined time period;
   measuring the current between the counter electrode and working electrode at least once during the third predetermined time period;
   determining the concentration of the analyte in the fluid test sample as a function of the current measured;
   calculating an index as a mathematical function of the following variables: a measured current of the first predetermined time period a recorded time of the first predetermined time period, and a measured current of the third predetermined time period;
   comparing the index to at least one predetermined parameter related to the determined concentration of analyte in the fluid test sample to identify when a bias, if any, exceeds a predetermined threshold; and
   displaying either an error signal or an analyte concentration depending on the comparison between the index and the at least one predetermined parameter.

2. The method of claim 1, wherein the analyte is glucose and the fluid test sample is a whole blood sample.

3. The method of claim 2, wherein the glucose concentration of the whole blood sample is determined using an amperometric monitoring system.

4. The method of claim 1, wherein the electrochemical sensor includes a base that provides a flow path for the fluid test sample and has on its surface the counter electrode and working electrode in electrical communication with an electrical current detector, a reaction layer on the surface of at least the working electrode comprising an enzyme that reacts with the analyte in the fluid test sample, and a lid adapted to mate with the base to form a space to receive the fluid test sample in which the counter and working electrodes are situated.

5. The method of claim 4, wherein the enzyme of the reaction layer is combined with a hydrophilic polymer.

6. The method of claim 4, wherein the enzyme is glucose oxidase.

7. The method of claim 1, wherein the electrochemical sensor includes an enzyme and a mediator in the enzyme, the mediator is a ferricyanide salt and is reduced in response to a reaction between the analyte and the enzyme.

8. The method of claim 1, wherein the first predetermined time-period is from about 2 to about 30 seconds.

9. The method of claim 8, wherein the first predetermined time period is from about 5 to about 15 seconds.

10. The method of claim 8, wherein the current is measured in regular intervals of from about 0.1 to about 3 seconds during the first predetermined time periods, and recording the time of such measurements.

11. The method of claim 10, wherein the current is measured in regular intervals of from about 0.2 and about 0.5 seconds, and recording the time of such measurements.

12. The method of claim 1, wherein the second predetermined time period is from about 2 to about 20 seconds.

13. The method of claim 12, wherein the second predetermined time period is from about 5 to about 15 seconds.

14. The method of claim 1, wherein the third predetermined time period is from about 2 to about 30 seconds.

15. The method of claim 14, wherein the third predetermined time period is from about 5 to about 15 seconds.

16. The method of claim 1, wherein the index (I) is calculated by solving the equation:

$$I=(I_{rt}/I_{bmax})*T_{bmax}$$

where
   $I_{rt}$=the last measurement of the current during the third predetermined time period,
   $I_{bmax}$=the highest current measured during the first predetermined time period, and
   $T_{bmax}$=the time of the highest measured current is measured during the first predetermined time period.

17. The method of claim 1, further including comparing the determined analyte concentration to at least one of the k-factor and read-to-burn ratio to assist in determining if an underfill condition is present.

18. The method of claim 1, wherein the error signal is displayed when the index is not within the at least one predetermined parameter.

19. The method of claim 1, wherein the concentration of the analyte is determined in the fluid test sample as a function of the current measured during the third predetermined time period.

20. The method of claim 1, wherein the method of determining the concentration of the analyte in the fluid test sample occurs in a disposable self-testing system.

21. The method of claim 1, wherein the method of determining the concentration of the analyte in the fluid test sample occurs in a clinical analyzer.

22. A method of determining the concentration of an analyte in a fluid test sample, the method comprising the acts of:
  providing an electrochemical sensor adapted to measure the analyte in the fluid test sample, the electrochemical sensor having a counter electrode and a working electrode;
  sufficiently covering the counter and working electrodes of the electrochemical sensor with the fluid test sample;
  applying a first potential between the counter electrode and working electrode for a first predetermined time period;
  measuring the current between the counter electrode and working electrode at least once during the first predetermined time period;
  recording the times of the at least one measurement during the first predetermined time period;
  removing or substantially reducing the first potential between the counter electrode and working electrode for a second predetermined time period;
  applying a second potential between the counter electrode and working electrode for a third predetermined time period;
  measuring the current between the counter electrode and working electrode at least once during the third predetermined time period;
  determining the concentration of the analyte in the fluid test sample as a function of the current measured;
  calculating an index (I) by solving the equation:

$$I = (I_{rt}/I_{bmax}) * T_{bmax}$$

where
    $I_{rt}$ = a selected measurement of the current during the third predetermined time period,
    $I_{bmax}$ = the highest current measured during the first predetermined time period, and
    $T_{bmax}$ = the time of the highest measured current is measured during the first predetermined time period;
  comparing the index to at least one predetermined parameter related to the determined concentration of analyte in the fluid test sample to identify when a bias, if any, exceeds a predetermined threshold; and
  displaying either an error signal or an analyte concentration depending on the comparison between the index and the at least one predetermined parameter.

23. The method of claim 22, wherein the analyte is glucose and the fluid test sample is a whole blood sample.

24. The method of claim 22, further including comparing the determined analyte concentration to at least one of a k-factor and read-to-burn ratio to assist in determining if an underfill condition is present.

25. The method of claim 22, wherein $I_{rt}$ is the last measurement of the current during the third predetermined time period.

26. A method of determining the concentration of an analyte in a fluid test sample, the method comprising the acts of:
  providing an electrochemical sensor adapted to measure the analyte in the fluid test sample, the electrochemical sensor having a counter electrode and a working electrode;
  sufficiently covering the counter and working electrodes of the electrochemical sensor with the fluid test sample;
  applying a first potential between the counter electrode and working electrode for a first predetermined time period;
  measuring the current between the counter electrode and working electrode at a plurality of times during the first predetermined time period;
  recording the time of at least one measurement during the first predetermined time period;
  removing or substantially reducing the first potential between the counter electrode and working electrode for a second predetermined time period;
  applying a second potential between the counter electrode and working electrode for a third predetermined time period;
  measuring the current between the counter electrode and working electrode at least one during the third predetermined time period, determining the concentration of the analyte in the fluid test sample as a function of the current measured;
  calculating an index as a mathematical function of the following variables: a recorded time of the first predetermined time period, and a measured current of the third predetermined time period;
  comparing the index to at least one predetermined parameter related to the determined concentration of analyte in the fluid test sample to identify when a bias, if any, exceeds a predetermined threshold; and
  displaying either an error signal or an analyte concentration depending on the comparison between the index and the at least one predetermined parameter.

27. The method of claim 26, wherein the analyte is glucose and the fluid test sample is a whole blood sample.

28. The method of claim 26, further including comparing the determined analyte concentration to at least one of a k-factor and read-to-burn ratio to assist in determining if an underfill condition is present.

* * * * *